United States Patent
Mestl et al.

(10) Patent No.: US 11,059,032 B2
(45) Date of Patent: Jul. 13, 2021

(54) SYNTHESIS OF A MOVNBTE SHELL CATALYST FOR OXIDATIVE DEHYDROGENATION OF ETHANE TO ETHYLENE

(71) Applicant: Clariant International Ltd, Muttenz (CH)

(72) Inventors: Gerhard Mestl, Munich (DE); Klaus Wanninger, Kolbermoor (DE); Silvia Neumann, Schechen (DE); Peter Schinke, Munich (DE)

(73) Assignee: CLARIANT INTERNATIONAL LTD, Muttenz (CH)

( * ) Notice: Subject to any disclaimer, the term of this patent is extended or adjusted under 35 U.S.C. 154(b) by 0 days.

(21) Appl. No.: 16/647,549

(22) PCT Filed: Sep. 13, 2018

(86) PCT No.: PCT/EP2018/074756
§ 371 (c)(1),
(2) Date: Mar. 16, 2020

(87) PCT Pub. No.: WO2019/057602
PCT Pub. Date: Mar. 28, 2019

(65) Prior Publication Data
US 2020/0215516 A1    Jul. 9, 2020

(30) Foreign Application Priority Data
Sep. 19, 2017    (DE) .................... 10 2017 121 709.6

(51) Int. Cl.
| | |
|---|---|
| *B01J 23/28* | (2006.01) |
| *B01J 6/00* | (2006.01) |
| *B01J 23/00* | (2006.01) |
| *B01J 35/10* | (2006.01) |
| *B01J 37/02* | (2006.01) |
| *C07C 5/48* | (2006.01) |
| *C07C 11/04* | (2006.01) |
| *C07C 51/215* | (2006.01) |
| *C07C 57/04* | (2006.01) |

(52) U.S. Cl.
CPC ............... *B01J 23/28* (2013.01); *B01J 6/001* (2013.01); *B01J 23/002* (2013.01); *B01J 35/1014* (2013.01); *B01J 35/1038* (2013.01); *B01J 37/0215* (2013.01); *C07C 5/48* (2013.01); *C07C 11/04* (2013.01); *C07C 51/215* (2013.01); *C07C 57/04* (2013.01); *C07C 2523/28* (2013.01)

(58) Field of Classification Search
CPC ........................................................ B01J 23/28
USPC ........................................................... 502/1
See application file for complete search history.

(56) References Cited

U.S. PATENT DOCUMENTS

| | | | |
|---|---|---|---|
| 5,281,745 A | 1/1994 | Ushikubo | |
| 5,380,933 A | 1/1995 | Ushikubo | |
| 6,867,328 B2 | 3/2005 | Borgmeier | |
| 7,005,403 B2 | 2/2006 | Borgmeier | |
| 7,009,075 B2 | 3/2006 | Hazin | |
| 7,038,080 B2 | 5/2006 | Dieterle | |
| 7,091,377 B2 | 8/2006 | Borgmeier | |
| 9,073,036 B2 | 7/2015 | Hagemeyer | |
| 2004/0097368 A1* | 5/2004 | Borgmeier | B01J 23/31 502/312 |
| 2008/0249328 A1* | 10/2008 | Kaduk | B01J 35/002 558/321 |
| 2014/0221683 A1* | 8/2014 | Welker-Nieuwoudt | B01J 23/8885 562/535 |

FOREIGN PATENT DOCUMENTS

| | | | |
|---|---|---|---|
| DE | 112009000404 | | 12/2010 |
| DE | 112009000364 | | 3/2011 |
| EP | 0318295 | | 5/1989 |
| JP | 07232071 | | 9/1995 |
| JP | 07053414 | | 9/1996 |
| WO | WO2004/035528 | * | 4/2004 |
| WO | 2008068332 | | 6/2008 |
| WO | 2009106474 | | 9/2009 |

OTHER PUBLICATIONS

Desanto, Peter, Structural aspects of the M1 and M2 phases . . . Z. Kristallogr. 219 (2004) 152-165.
Valente, Jamie S., Chemical, Structural, and Morphological Changes of a MoVTeNb catalyst . . . ACS Catal. 4, (2014) 1292-1301.
Sanfiz, A. Celaya, Preparation of Phase-Pure M1 MoVTeNb Oxide . . . Top. Catal. 50, (2008) 9-32.
Ushikubo, Takashi Ammoxidation of propane over Mo—V—Nb—Te mixed oxide catalysts, Studies in Surface Science and Catalysis 112 (1997) 473-480.
P. Botella, Solid State Science 7 (2005) 507-519 "MoVTeNbO multifunctional catalysts: Correlation . . . ."
Hiromu Watanabe, Applied Catal. A General, 194-195 (2000) 479-485 "New synthesis route for . . . ."
Chu, Bozhao, Applied Cataysis A: General 524 (2016) 56-65 "Phase-pure MIMoVNbTeOxcatalysts with tunable particle size fo oxidative dehydrogenation of ethane".

* cited by examiner

*Primary Examiner* — Douglas B Call

(57) ABSTRACT

A novel coated catalyst having an outer shell which is composed of a catalyst material having high surface area and contains molybdenum, vanadium, tellurium and niobium, and the use of this catalyst for the oxidative dehydrogenation of ethane to ethene or the oxidation of propane to acrylic acid and also a process for producing the catalyst is disclosed.

14 Claims, No Drawings

SYNTHESIS OF A MOVNBTE SHELL CATALYST FOR OXIDATIVE DEHYDROGENATION OF ETHANE TO ETHYLENE

The invention relates to a novel coated catalyst having an outer shell which is composed of a catalyst material having high surface area and contains molybdenum, vanadium, tellurium and niobium, and the use of this catalyst for the oxidative dehydrogenation of ethane to ethene or the oxidation of propane to acrylic acid and also a process for producing the catalyst.

MoVNbTe mixed oxides for the oxidation of propane to acrylic acid or for the oxidative dehydrogenation of ethane to ethene are prior art. More than 200 patents and numerous scientific publications are concerned with catalysts based on MoVNbTe mixed oxides. Promotion of these mixed oxides with other metals of the Periodic Table is known. Here, the highest previously described acrylic acid yields are 60% and those of ethene are about 80%.

The MoVNbTe basis system based on four elements for a catalyst was first proposed by Mitsubishi for the ammoxidation of propane to acrylonitrile (1989, EP 318295 A1) and the oxidation to acrylic acid (1994, EP 608838 A2). JP H07-053414 (Mitsubishi) discloses a catalytic process for preparing ethylene by oxidative hydrogenation of ethane at low temperature, in high yield and with high selectivity. This process for preparing ethylene comprises contacting ethane with a gas containing molecular oxygen in the presence of a catalyst composition at elevated temperature, where the catalyst composition contains a mixed metal oxide which has molybdenum, vanadium, tellurium and oxygen as main components and displays an X-ray powder diffraction pattern which has essentially the following relative peak intensities: 2θ (+−0.4°), rel. int.: 22.1° (100), 28.2° (400~3), 36.2° (80~3), 45.1° (40~3), 50° (50~3).

MoVNbTe catalysts consist mainly of two orthorhombic phases which are referred to as "M1" and "M2" (T. Ushikubo, K. Oshima, A. Kayou, M. Hatano, Studies in Surface Science and Catalysis 112, (1997), 473).

The M1 phase appears to play the important role in the selective oxidation reactions.

According to P. De Santo et al., Z. Kristallogr. 219 (2004) 152, the main phases M1 and M2 in MoVNbTe mixed oxides for the selective oxidation can be described, for example, by the following structural formulae:

M1: 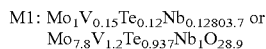
$Mo_{7.8}V_{1.2}Te_{0.937}Nb_1O_{28.9}$

M2:*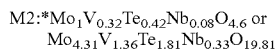
$Mo_{4.31}V_{1.36}Te_{1.81}Nb_{0.33}O_{19.81}$

The two main phases can also occur with a somewhat different stoichiometry. Both vanadium and molybdenum are present in the center of an octahedron of oxygen atoms and are therefore partly exchangeable in the structure, so that the same structure, e.g. the M1 phase, is also possible with a higher vanadium content. A detailed study of these relationships may be found in P. Botella et al., Solid State Science 7 (2005) 507-519. The M2 phase in particular is not active for oxidative dehydrogenation of ethane (see J. S. Valente et al., ACS Catal. 4(2014), 1292-1301, especially p.1293). A catalyst consisting of a very pure M1 phase is therefore desirable for the oxidative dehydrogenation of ethane. Attempts are therefore made to produce these crystal phases cleanly and separately.

EP 529853 A2 discloses a catalyst which is suitable for preparing a nitrile from an alkane, wherein the catalyst has the empirical formula $MoV_bTe_cX_xO_n$, where X is at least one of Nb, Ta, W, Ti, Al, Zr, Cr, Mn, Fe, Ru, Co, Rh, Ni, Pd, Pt, Sb, Bi, B and Ce, b is from 0.01 to 1.0, c is from 0.01 to 1.0; x is from 0.01 to 1.0 and n is a number by means of which the total valence of the metallic elements is satisfied and the catalyst has X-ray diffraction peaks at the following 2θ angles in its X-ray diffraction pattern: diffraction angle at 2θ (22.1°+/−0.3°, 28.2°+/−0.3°, 36.2°+/−0.3°, 45.2°+/−0.3°, 50.0°+/−0.3°).

JP H07-232071 discloses a catalytic process for preparing a nitrile at a relatively low temperature and in a high yield, using an alkane as raw material and a particular catalyst. The main component of the catalyst is a mixed metal oxide composed of molybdenum, vanadium, tellurium, oxygen and X (X is one or more elements selected from the group consisting of niobium, tantalum, etc.), where the ratio of the main components, i.e. with the exception of oxygen, is expressed by the formulae I to IV: I) 0.25<rMo<0.98, II) 0.003<rV<0.50, III) 0.003<rTe<0.50, IV) 0≤rX<0.5, (rMo, rV, rTe and rX are in each case the molar parts of molybdenum, vanadium, tellurium and X) and in the XRD XRD bands of this mixed oxide appear at the various 2θ angles 9.0°±0.3°, 22.1°±0.3°, 27.3°±0.3°, 29.2°±0.3° and 35.4°±0.3°. According to this document, a nitrile can be prepared in high yield at low temperature by reacting an alkane without the presence of a halogenated substance, e.g. with water, etc., in the reaction system.

Other successful attempts to produce a pure M1 phase are based on dissolving the M2 phase out from the phase mixture. These experiments are described, for example, in EP 1301457 A2, EP 1558569 A1 or WO 2009106474 A2.

A. C. Sanfiz et al., Top. Catal. 50 (2008) 19-32, describe hydrothermal syntheses of MoVNbTe oxide. These syntheses start out exclusively from soluble compounds. Telluric acid $Te(OH)_6$ is generally used as soluble compound of tellurium. In the most readily available oxidic tellurium compound $TeO_2$, tellurium has the oxidation state +4. Unfortunately, tellurium dioxide ($TeO_2$) is sparingly soluble in water. However, the tellurium in telluric acid has the oxidation state +6. Tellurium therefore has to be oxidized up in the preparation of telluric acid. The most widespread synthesis is carried out by oxidation of tellurium oxide with hydrogen peroxide, which on a large scale is accompanied by safety problems because hydrogen peroxide can disproportionate into water and oxygen in a spontaneous decomposition. For this reason, telluric acid can be prepared in large amounts only with difficulty. The Nb component used in the synthesis of MoVNbTe mixed oxides is generally ammonium niobium oxalate. Niobium oxide, on the other hand, is sparingly soluble and therefore has only limited suitability as starting compound.

Watanabe (Applied Catal. A General, 194-195 (2000) 479-485) describes, inter alia, the hydrothermal synthesis from the sparingly soluble precursors $MoO_3$, $V_2O_5$ and $TeO_2$. The hydrothermal synthesis gives a precursor for an ammoxidation catalyst which compared to a catalyst produced by the known dry method has twice the activity after calcination. The mixed oxides produced by the solid-state reaction display a rather low activity. It has been proposed that the higher activity of the catalyst produced by the hydrothermal synthesis is due first and foremost to the higher surface area.

WO 2013021034 A1 relates to a catalyst material for the oxidation and/or oxidative dehydrogenation of hydrocarbons, in particular for the selective oxidation of propane to acrylic acid, comprising a) molybdenum (Mo), b) vanadium (V), c) niobium (Nb), d) tellurium (Te), e) manganese (Mn)

and cobalt (Co), wherein the molar ratio of at least one element selected from among manganese and cobalt to molybdenum is in the range from 0.01 to 0.2, more preferably from 0.02 to 0.15 and particularly preferably from 0.03:1 to 0.1:1. Furthermore, a catalyst for the oxidation and/or oxidative dehydrogenation of hydrocarbons, a use of the catalyst material or of the catalyst, a process for producing a catalyst material for the oxidation and/or oxidative dehydrogenation of hydrocarbons and a process for the selective oxidation of propane to acrylic acid are disclosed.

WO 2008068332 A1 relates to novel, mesoporous mixed metal oxide catalysts and a process for the production thereof and also the use thereof as catalyst for the oxidation of hydrocarbons or partially oxidized hydrocarbons. In particular, the disclosure relates to mesoporous mixed oxide catalysts which contain at least two, preferably at least three, different metal species, with at least one thereof belonging to the group of the transition metals, to a process for the production thereof, to such a catalyst comprising a production step via the "neutral template" route and a calcination step in an essentially oxygen-free atmosphere at a temperature in the range from 300 to 700° C. and to the use of such catalysts as oxidation catalysts for the preparation of oxidized hydrocarbons and in particular for the selective oxidation or ammoxidation of propane to acrylic acid and acrylonitrile. A preferred catalyst comprises the elements Mo, V, Te and Nb.

WO 0232571 A1 describes a coated catalyst whose shell composed of active material is a multimetal oxide containing the elements Mo, V and Te and/or Sb and which is intended as catalyst for the heterogeneous catalyzed gas-phase oxidation of propane to acrylic acid.

In all the syntheses of the M1 phase described in the prior art, the M1 phase is formed only in a high-temperature treatment, typically at above 500° C. under inert gas, ("activation") after the reaction of the starting materials. Such catalysts according to the prior art then usually have BET surface areas of from 4 to 20 m$^2$/g.

MoVNbTe mixed oxide catalysts have been able to be pressed to form particles and used in large industrial reactors. For this purpose, specific geometries of the particles were found to be particularly advantageous; rings display, for example, a lower pressure drop than solid, cylindrical pellets. The disadvantage here is that the pressed particles consist entirely of active composition (all-active catalysts) and correspondingly large amounts of the expensive elements niobium and tellurium have to be used. There is therefore a need for coated catalysts which have active composition only on the surface and in the interior consist of an inert support. However, a prerequisite for the production of such coated catalysts is a high activity of the active composition, so that it can, in comparison with the all-active catalyst, achieve a comparable catalytic reaction with a smaller amount of active composition.

It was an object of the present invention to find a highly active coated catalyst based on this mixed oxide material which comprises the elements molybdenum, vanadium, tellurium and niobium ("MoVTeNb mixed oxide") and comprises the M1 phase and has a very large specific surface area. A further object of the invention was to provide a coated catalyst for the oxidation of alkanes which has a very high activity when using a very low mass of MoVTeNb mixed oxide. The latter is important since MoVNbTe mixed oxide is very expensive, in particular because of the rare metals Te and niobium.

The object is achieved by a coated catalyst comprising an inert support and a catalytically active outer shell which comprises a mixed oxide material comprising the elements molybdenum, vanadium, niobium and tellurium (MoVNbTe mixed oxide), characterized in that the catalyst has a BET surface area of more than 30 m$^2$/g.

The coated catalyst according to the invention is produced by a process comprising the steps:
  a) production of a mixture of starting compounds, which contains molybdenum, vanadium, niobium and a tellurium-containing starting compound in which tellurium is present in the oxidation state +4 and also oxalic acid and at least one further oxo ligand,
  b) hydrothermal treatment of the mixture of starting compounds at a temperature of from 100 to 300° C., to give a product suspension,
  c) isolation and drying of the mixed oxide material present in the product suspension resulting from step b),
  d) optionally calcination of the mixed oxide material (MoVTeNb mixed oxide) obtained in step c) under inert gas at from 300 to 450° C.,
  e) production of a coating suspension containing the mixed oxide material from step d) with addition of organic and/or inorganic binders,
  f) coating of an inert catalyst support with the coating suspension from step e) by spraying the coating suspension into an agitated bed of the inert catalyst supports and optionally
  g) calcination of the catalyst particles from step f) at a temperature of from 80 to 400° C.

Step g) can optionally be carried out in the production of the catalyst or only in the reactor in which the catalytic reaction is carried out before use in the catalytic reaction.

The starting compounds are the molybdenum-, vanadium-, tellurium- and niobium-containing starting materials of the hydrothermal synthesis (precursor compounds). These in each case contain one or more of the elements molybdenum, vanadium, tellurium or niobium.

The molybdenum-containing starting compound can, for example, be an ammonium heptamolybdate or molybdenum trioxide, the vanadium-containing starting compound can, for example, be an ammonium metavanadate, vanadyl sulfate or vanadium pentoxide, and the niobium-containing starting compound can, for example, be ammonium niobium oxalate or niobium oxalate or niobium oxide. The tellurium-containing starting compound according to the invention is one in which tellurium is present in the oxidation state +4, i.e. as tellurium(IV) cation, as in tellurium dioxide or a compound of the formula $M_x^{n+}TeO_3$ (where n=1 or 2 and x=2/n), where M is an alkali metal or alkaline earth metal, e.g. $Na_2TeO_3$. The tellurium-containing starting compound is particularly preferably tellurium dioxide which can be present in any degree of hydration.

The inert catalyst support can consist of aluminum oxide, silicon dioxide, zirconium oxide or mixed oxides of the elements, e.g. ceramic such as steatite, or of silicon carbide. The shaped support body particularly preferably consists of inert oxides having a very low specific BET surface area and no internal porosity, e.g. steatite, alpha-aluminum oxide, silica (silicon dioxide), mullite or cordierite.

One aspect of the production process of the invention is that a synthesis of the M1 phase can be successfully carried out from the insoluble and inexpensive oxides, e.g. $MoO_3$, $V_2O_5$, $Nb_2O_5$ and $TeO_2$, and a combination of oxalic acid with at least one further oxo ligand. As further oxo ligands (i.e. in addition to the oxalic acid), dicarboxylic acids and diols have been found to be particularly suitable, as have organic compounds having two adjacent carbon atoms which each bear a hydroxy group. Particular preference is given to using a mixture of citric acid and glycol as further oxo ligand. The oxalic acid should preferably be present in the mixture of the starting compounds in an Mo/oxalic acid ratio of from 1:0.01 to 1:1, preferably from 1:0.08 to 1:0.4, more preferably from 1:0.15 to 1:0.25. The at least one further oxo ligand, or all further oxo ligands together, should preferably be present in the mixture of the starting compounds in an Mo/oxo ligand ratio of from 1:0.01 to 1:1, preferably from 1:0.025 to 1:0.2, more preferably from 1:0.05 to 1:0.1.

If metal oxides in powder form are used as starting compounds, the $D_{50}$ of the respective metal oxide used is less than 10 μm. Should the metal oxide powders have particles which are too large, these have to be milled beforehand, either wet or dry, until their $D_{50}$ values are <10 μm.

The synthesis according to the invention surprisingly gives the M1 phase straight after the hydrothermal synthesis and drying. Subsequent calcination under nitrogen at from 300 to 400° C. gives a catalyst having a surface area of greater than 30 $m^2/g$.

A further advantage of the synthesis according to the invention of the M1 phase is the completely surprising, high efficiency of the conversion of the starting materials by the hydrothermal synthesis. If the stoichiometry of the starting materials is in the range Mo/V/Nb/Te=1:0.22:0.1:0.1 to 1:0.3:0.17:0.17, Mo, V, Nb and Te are converted virtually completely into M1 phase, so that less than 100 ppm of all metals remain in the mother liquor.

The possible stoichiometry of the M1 phase is adequately known from the literature and can be represented by the formula $Mo_1V_aNb_bTe_cO_x$ where a=0.2 to 0.3, b=0.05 to 0.2, c=0.05 to 0.25 and x is a variable which leads, as a function of the oxidation state of the metals (Mo, V, Nb and Te), to charge balance.

The mixture of starting compounds for the hydrothermal synthesis is preferably present as aqueous suspension and is subsequently treated hydrothermally. The term "hydrothermally" refers predominantly to reaction conditions for producing a catalyst material in the presence of water and at elevated temperature and/or elevated pressure, for example in an autoclave. Here, the pressure can be in the range from 5 to 30 bar, preferably from 10 to 27 bar. Illustrative pressure ranges are from 11 to 20 bar.

As a result of the hydrothermal treatment (step b)), a product suspension containing the MoVNbTe mixed oxide as solid is obtained. In the process of the invention, the isolation of the solid of the suspension in step c), which represents the MoVNbTe mixed oxide, can be carried out in one or more filtration steps, e.g. filtering-off of the mother liquor. Drying can be carried out in one step or a plurality of, preferably two, steps in flowing or static air. The first drying step is preferably carried out at from 60° C. to 150° C. (particularly preferably from 80° C. to 120° C.), and a second drying step can be carried out at from 200 to 400° C. In addition, step c) of the process of the invention can comprise one or more washing steps, calcination steps (thermal treatment) and/or milling steps. Calcination can be carried out at from 200° C. to 450° C., preferably from 300° C. to 400° C., in inert gas.

To produce the coated catalyst, a coating suspension is firstly produced from the MoVNbTe mixed oxide with addition of a solvent, preferably water. This coating suspension then contains organic and/or inorganic binders. Possible organic binders are, for example, polymers or emulsions of the polymers polyvinyl acetate, ethylene-vinyl acetate, poly-acrylates and other acrylate copolymers. Possible inorganic binders are, for example, sols of silicon dioxide, zirconium oxide or titanium dioxide.

This coating suspension is applied to the inert support in order to form the catalytically active outer shell. This application is preferably effected by spraying-on. Coating is particularly preferably carried out by spraying the suspension into an agitated bed of inert catalyst support bodies. The coated catalyst support bodies are subsequently dried and optionally calcined, with any organic binders present being burnt out. However, this treatment can also be carried out in the reactor in which the coated catalyst is used, before the actual start-up is carried out.

The coated catalyst preferably has a catalytically active outer shell having a layer thickness in the range from 200 to 400 μm.

The coated catalyst of the invention can be used as catalyst for the oxidation and/or oxidative dehydrogenation ("ODH") of hydrocarbons, in particular for the oxidative dehydrogenation of ethane to ethylene.

Methods of Characterization:

To determine the parameters of the catalysts according to the invention, the following methods are used:

1. BET Surface Area

The determination of the BET surface area of the shaped catalyst bodies was carried out by the BET method in accordance with DIN 66131; a publication of the BET method may also be found in J. Am. Chem. Soc. 60,309 (1938). The measurements were carried out on a TriStar from Micromeritics at 77 K. The sample was evacuated for 2 hours at 523 K before the measurement. The linear regression of the isotherms according to the BET method was carried out in a pressure range of $p/p_0$=0.01-0.3 ($p_0$=730 torr).

2. $N_2$ Pore Distribution

The determination of the pore size distribution of a catalyst powder was carried out by means of nitrogen sorption measurements on a TriStar from Micromeritics at 77 K. The sample was evacuated for 2 hours at 523 K before the measurement. Both adsorption and desorption isotherms were determined and employed for the evaluation by the Barrett-Joyner-Halenda method (BJH).

3. Hg Pore Volume

The pore distribution and the pore volume of the catalyst particles (pellets and coated rings as coated catalysts) were determined using a mercury porosimeter: Pascal 440 from Thermo Electron Corporation in accordance with DIN 66133. Here, the sample was evacuated beforehand for 30 minutes at room temperature. Samples in the range from 600 to 900 mg were measured and the pressure was increased up to 2000 bar.

Pellets consist entirely of porous material, so that the pore volume is always to be based on the total measured pellet.

Coated catalysts have a support material, which generally has approximately no internal surface area (BET surface area ~0 $m^2/g$) and approximately no pore volume (pore volume ~0 $cm^3/g$), in their interior.

However, since the mass of the inert support is here included in the weighing and determination for the measurement, the final values are based on the entire coated catalyst, not on the catalytically active outer shell. In order to base the measured pore volume in $cm^3/g$ on the catalytically active outer shell, the pore volume determined has to be divided by the proportion (by mass) of the porous layer in the total mass.

WORKING EXAMPLES

The invention will be illustrated by the following non-limiting working examples.

Comparative Example 1 describes an MoVTeNb catalyst which was activated according to the prior art at 600° C. and pressed by customary methods with addition of customary tabletting additives such as graphite and stearic acid to give pellets.

Comparative Example 1

68.25 g of $TeO_2$ (Alfa Aesar) and 200 g of distilled $H_2O$ were firstly weighed together into the $ZrO_2$-coated milling vessel and milled in a planetary ball mill using 50 1 cm balls ($ZrO_2$) at 400 rpm for 1 hour. The milled slurry 1 was subsequently transferred together with 500 ml of distilled $H_2O$ into a 2 l glass beaker. 56.83 g of $Nb_2O_5$ and 200 g distilled $H_2O$ were weighed together into the $ZrO_2$-coated milling vessel and milled in the same ball mill under identical conditions to the $TeO_2$. This milled slurry was subsequently transferred together with 500 ml of distilled $H_2O$ into a second 2 l glass beaker for 2 hours. After 20 hours, the mixture was heated to 80° C. and 107.8 g of oxalic acid dihydrate was added to the $Nb_2O_5$ suspension 2. The slurry 3 is formed and was stirred for approximately 1 h using a magnetic stirrer. 6 l distilled $H_2O$ were placed in an autoclave (40 l) and heated to 80° C. while stirring. After the water had attained the temperature, 61.58 g of citric acid, 19.9 g of ethylene glycol, 615.5 g of $MoO_3$ (Sigma Aldrich $D_{50}$=13.0 μm), 124.5 g of $V_2O_5$, the milled $TeO_2$ (slurry 1) and the milled $Nb_2O_5$ in oxalic acid (slurry 3) were added in succession. 850 ml of distilled $H_2O$ were used for transfer into the autoclave and rinsing of the vessels. The total amount of water in the autoclave was 8.25 l (speed of the stirrer 90 rpm). After the autoclave had been closed, the contents were blanketed with nitrogen under slightly superatmospheric pressure (4 bar) for 5 minutes. A hydrothermal synthesis was carried out in the 40 l autoclave at 190° C. for 48 l (heating time 3 h). After the synthesis (suspension has a temperature of less than 50° C.), the suspension was filtered under reduced pressure through a blue band filter and the filter cake was washed with 5 l of distilled $H_2O$. The precursor material P1 was produced in this way. P1 was subsequently dried at 80° C. for 3 days in a drying oven. The precursor material P2 was produced in this way. P2 was subsequently milled in a beater mill. The precursor material P3 was produced in this way.

Solids yield: 0.8 kg

P3 was then calcined under the following conditions: heating rate 5° C./min, 280° C./4 h, air flow: 1 l/min. A precursor material P4 was produced in this way.

P4 was then activated under the following conditions: activation was carried out at 650° C. for 2 hours (heating rate 10° C./min) under $N_2$ (0.5 l/min) in a retort in a furnace. The catalyst K1 was produced in this way.

The catalyst K1 has a BET surface area of 9 m²/g and an $N_2$ pore volume of 0.04 cm³/g.

This powder K1 was then used to produce catalyst pellets K2. For this purpose, 473 g of the powder K1 were intimately mixed with 9.65 g of graphite, 54.96 g of stearic acid and 54.96 g of fine silicon dioxide (Syloid C809). The catalyst powder K3 was produced in this way.

The catalyst powder K3 was granulated twice (i.e. pressed and once again comminuted through a sieve to give a granular material comprising particles in the range of about 30-400 μm, using a Powtec roller compactor). The catalyst granules K4 were produced in this way. The catalyst granules K4 were tableted in a tableting press (Rotab) using a pressing pressure of about 11 kN to give rings (diameter 5.4 mm, height 5 mm, internal diameter 2.5 mm). The shaped catalyst body K5 was produced in this way.

After tableting, the stearic acid was burnt out from the shaped catalyst body K5 at 350° C. in air in a Nabertherm convection oven using a slow heating rate (<1° C./10 min). The comparative catalyst K6 was produced in this way.

Comparative Example 2 describes a comparative catalyst in the case of which the catalyst powder was produced by the process of the invention but was tabletted in the same way as Comparative Example 1.

Comparative Example 2

116.06 g of $TeO_2$ (Alfa Aesar) were firstly slurried in 1000 g of distilled $H_2O$ by means of a precision glass stirrer and milled in a MicroCer ball mill (Netsch) using 0.8 mm balls ($ZrO_2$). The portion was subsequently transferred together with 750 ml of distilled $H_2O$ into a glass beaker and stirred by means of a magnetic stirrer. 96.64 g of $Nb_2O_5$ and 183.35 g of oxalic acid dihydrate were slurried in 1000 g of distilled $H_2O$ by means of a precision glass stirrer and milled in the same ball mill. The portion was subsequently transferred together with 750 ml of distilled $H_2O$ into a 3 l glass beaker and stirred by means of a magnetic stirrer. After 20 hours, both suspensions were heated to 80° C. and stirred for about 1 hour. 1046.7 g of $MoO_3$ (Sigma Aldrich; somewhat larger particles) were suspended in 8.5 l of water and likewise milled quickly by means of this ball mill ($D_{50}$=12.7 μm). This 8.5 l of $MoO_3$ suspension were placed in an autoclave (40 l) and heated to 80° C. while stirring. After the water had attained the temperature, 14.61 g of citric acid, 33.85 g of ethylene glycol, 211.61 g of $V_2O_5$, the milled $TeO_2$ and the milled $Nb_2O_5$ in oxalic acid were added in succession. The total amount of water in the autoclave was 14 l (speed of the stirrer 90 rpm). After the autoclave had been closed, the contents were blanketed with nitrogen under slightly superatmospheric pressure (4 bar) for 5 minutes. A hydrothermal synthesis was carried out in the 40 l autoclave at 190° C./48 h (heating time 3 h). After the synthesis (i.e. when the suspension has a temperature of less than 50° C.), the suspension was filtered under reduced pressure through a blue band filter and the filter cake was washed with 5 l of distilled $H_2O$. The filter cake was then dried at 80° C. in a drying oven for 3 days and subsequently milled in a beater mill. The solids yield was 0.8 kg.

The solid was subsequently activated: it was calcined at 400° C./2 h (heating rate 10° C./min) under $N_2$ (0.5 l/min) in a retort in a furnace.

The activated solid has a BET surface area of 27 m²/g and an $N_2$ pore volume of 0.116 cm³/g.

This powder was used to produce catalyst pellets. These pellets were produced as described in Comparative Example 1.

Example 3 describes the catalyst according to the invention in the case of which only 20% by weight of catalyst composition were applied to an inert support.

Example 1

116.06 g of $TeO_2$ (Alfa Aesar) were firstly slurried in 250 g of distilled $H_2O$ and milled in a ball mill. The portion was subsequently transferred together with 7500 ml of distilled $H_2O$ into a glass beaker. 96.64 g of $Nb_2O_5$ were slurried into 250 g of distilled $H_2O$ and milled in a ball mill. The portion was subsequently transferred with 500 ml of distilled $H_2O$ into a glass beaker. Next morning, the mixture was heated to 80° C., 183.35 g of oxalic acid dihydrate was added to the $Nb_2O_5$ suspension and the mixture was stirred for about 1 hour. 1046.7 g of $MoO_3$ (Sigma Aldrich) were suspended in 8.5 l of water and milled ($D_{50}$=2.9 μm) using a MicroCer ball mill for 4 hours with circulation. This 8.5 l of $MoO_3$ suspension was placed in an autoclave (40 l) and heated to 80° C. while stirring. After the water had attained the temperature, 14.61 g of citric acid, 33.85 g of ethylene glycol, 211.61 g of $V_2O_5$, the milled $TeO_2$ and the milled $Nb_2O_5$ in oxalic acid were added in succession. The total amount of water in the autoclave was 14 l (speed of the stirrer 90 rpm). The contents of the autoclave were subsequently blanketed with nitrogen. A hydrothermal synthesis was carried out in the 40 l autoclave at 190° C./48 h. After the synthesis, the mixture was filtered under reduced pressure through a blue band filter and the filter cake was washed with 5 l of distilled $H_2O$. The filter cake was subsequently dried at 80° C. in a drying oven for 3 days and subsequently milled in a beater mill (small IKA laboratory mill). The solids yield was 1.4 kg.

The solid obtained was subsequently calcined: calcination was carried out at 400° C./2 h, (heating rate 10° C./min) under N2 (0.5 l/min) in a retort in a furnace.

The activated solid has a BET surface area of 50 m²/g and an N2 pore volume of 0.27 cm³/g.

This powder was then used to produce a coating suspension. For this purpose, 181 g of the powder were suspended in 1047 g of water, and 39.93 g of Bindzil 2034DI silica sol, 4.52 g of Syloid C809 and 13.57 g of Coconit were added. This suspension was homogenized using an Ultra-Turrax stirrer (5 min/6000 rpm). 54.30 g of EP16 vinyl acetate adhesive from Wacker was subsequently added and the total mixture was then stirred for 1 hour by means of a magnetic stirrer. 600 g of steatite rings (4 mm diameter, 2 mm internal diameter, 4 mm height) were then coated with the coating suspension in a coating plant from Hüttlin. Here, the bed of the rings was set into rotating motion by means of an air stream of from 198 m³/h to 260 m³/h (70° C.) from below through oblique slots in a plate. The coating suspension was sprayed through nozzles into this rotating bed (0.3 bar). (Coating loss via the air stream: 14.5%; proportion of the porous layer (silica+catalyst): 21.5%; proportion of the active composition: 19.2%)

From 380 to 420 ml (373 g of pellets or 460 g of coated rings) were introduced into a tube reactor heated by means of a salt bath (diameter 2.54 cm, length 1 m, isothermally heated zone 80 cm).

The catalyst was heated to 290° C. under a stream of nitrogen. Steam, air and subsequently ethane were then additionally introduced until the following flow rates had been achieved: $N_2$=48 sl/h; water=0.7 ml/min (reported as liquid, water was vaporized); air=35.3 sl/h and ethane 13.7 sl/min. The salt bath temperature was then increased in steps of 2° C. to the temperatures listed in Table 1 (the unit [sl] corresponds to the standard liter, i.e. one liter at 1.0133 bar and 0° C.)

The inlet gas compositions and the outlet gas compositions were analyzed. For this purpose, a substream was drawn off through heated conduits by means of a vacuum pump. This analysis substream was firstly drawn through a sample valve of a GC, through a gas cooler and then dried and through an NDIR analyzer (from Rosemount). In the GC, ethane, ethene, acetic acid and water were analyzed by means of an Rt U-BOND column having a temperature profile of from 45° C. to 190° C. in 8.4 minutes at a gas flow of 10 ml/min. The NDIR analyzer (Rosemount) contains NDIR cells for CO, $CO_2$, ethane, ethene and also a paramagnetic oxygen sensor.

The conversion of ethene was calculated by comparison of the inlet and outlet gas compositions and is shown in Table 1.

It can be seen from the results in Table 1 that the catalyst of Comparative Example 2 is significantly more active than the comparative catalyst 1 according to the prior art at 330° C., since it achieves the same ethane conversion of 67% at as low as 302° C. The salt bath temperature for the catalyst of Comparative Example 2 cannot be set to 330° C. since an uncontrolled temperature rise in the exothermic reaction ("runaway reaction") is observed under these conditions. For this reason, the catalyst of Comparative Example 2 cannot be utilized optimally.

The catalyst of Example 3 according to the invention, on the other hand, has only 20% of the active mass in the same reactor volume and achieves an ethane conversion of 50% at 330° C.

TABLE 1

| Exp. | $T_{Max}$ in calcination [° C.] | BET of the powder catalysts [m²/g] | N2 pore volume of the powder catalysts [cm³/g] | Cat. shape Ø external [mm] | Proportion of active composition [%] | BET surface area of catalyst particles [m²/g] | Hg pore volume of catalyst particles [cm³/g] | Salt bath temperature in ODH [° C.] | Ethane conversion [%] |
|---|---|---|---|---|---|---|---|---|---|
| Comp. 1 | 600 | 9 | 0.037 | pellet 5.4 | 90 | 44 | 0.23 | 330° C. | 67 |
| Comp. 2 | 400 | 27 | 0.12 | pellet 5.4 | 90 | 57 | 0.28 | 302° C. | 63 |
| Ex. 1 | 400 | 50 | 0.27 | coated 4 | 19.2 | 65 | 0.115 (coating 0.54) | 345° C. 330° C. | 64 50 |

After coating of the shaped catalyst support bodies, the vinyl acetate adhesive was burnt out at 320° C. in air in a furnace.

Example 2 describes a test for catalytic activity in the oxidative dehydrogenation of ethane to ethylene at various temperatures.

Example 2

The catalysts were tested in a test for activity in the oxidative dehydrogenation of ethane.

Table 1 compares the BET surface areas and the pore volumes of the catalyst according to the invention of Example 3 with the other comparative examples.

The invention claimed is:

1. A coated catalyst comprising an inert support and a catalytically active outer shell which comprises a mixed oxide material of the formula $Mo_iV_aNb_bTe_cO_x$ present in an M1 phase, where a is 0.2-0.3, b is 0.05-0.2, c is 0.05-0.25, and x is selected such that the overall charge of the empirical formula is zero; wherein the coated catalyst has a BET surface area of more than 30 m$^2$/g.

2. The coated catalyst as claimed in claim 1, wherein the coated catalyst has a mercury pore volume of greater than 0.1 cm$^3$/g.

3. The coated catalyst as claimed in claim 1, wherein the coated catalyst has a mercury pore volume in the shell of greater than 0.2 cm$^3$/g, based on the mass of the shell.

4. The coated catalyst as claimed in claim 1, wherein the inert support is selected from the group consisting of silicon oxide, aluminum oxide, steatite, mullite and cordierite.

5. The coated catalyst as claimed in claim 1, wherein the coated catalyst has a catalytically active outer shell having a layer thickness in the range from 200 to 400 µm.

6. A process for producing a coated catalyst as claimed in claim 1, comprising the steps:
  a) production of a mixture of starting compounds, which contains molybdenum, vanadium, niobium and a tellurium-containing starting compound in which tellurium is present in the oxidation state+4 and also oxalic acid and at least one further oxo ligand,
  b) hydrothermal treatment of the mixture of starting compounds at a temperature of from 100 to 300° C., to give a product suspension,
  c) isolation and drying of the mixed oxide material present in the product suspension resulting from step b),
  d) optionally calcination of the mixed oxide material obtained in step c) under inert gas at from 300 to 450° C.,
  e) production of a coating suspension containing the mixed oxide material from step d) with addition of organic and/or inorganic binders,
  f) coating of an inert catalyst support with the coating suspension from step e) by spraying the coating suspension into an agitated bed of the inert catalyst supports and optionally
  g) calcination of the catalyst particles from step f) at a temperature of from 80 to 400° C.

7. The process as claimed in claim 6, wherein the tellurium-containing starting compound is tellurium dioxide or a compound of the formula $M_x^{n+}TeO_3$ (where n=1 or 2 and x=2/n) where M is an alkali metal or an alkaline earth metal.

8. The process as claimed in claim 6, wherein the mixture of starting compounds is present as an aqueous suspension.

9. The process as claimed in claim 6, wherein the mixture of starting compounds contains a dicarboxylic acid, a diol or another compound having two hydroxy groups in adjacent positions as further oxo ligand.

10. The process as claimed in claim 6, wherein the mixture of starting compounds contains molybdenum trioxide.

11. The process as claimed in claim 6, wherein the mixture of starting compounds contains vanadium pentoxide.

12. The process as claimed in claim 6, wherein the mixture of starting compounds contains citric acid as further oxo ligand.

13. The process as claimed in claim 6, wherein the mixture of starting compounds contains citric acid and glycol as further oxo ligands.

14. A catalyst powder comprising
a mixed oxide material of the formula
$Mo_iV_aNb_bTe_cO_x$
present in an M1 phase, where a is 0.2-0.3, b is 0.05-0.2, c is 0.05-0.25, and x is
selected such that the overall charge of the empirical formula is zero; wherein the catalyst powder has a BET surface area of more than 30 m$^2$/g.

* * * * *